US006126086A

United States Patent [19]

Browner et al.

[11] Patent Number: 6,126,086

[45] Date of Patent: Oct. 3, 2000

[54] OSCILLATING CAPILLARY NEBULIZER WITH ELECTROSPRAY

[75] Inventors: Richard F. Browner; Zhenyu Shou, both of Atlanta, Ga.

[73] Assignee: Georgia Tech Research Corp., Atlanta, Ga.

[21] Appl. No.: 08/986,228

[22] Filed: Dec. 5, 1997

Related U.S. Application Data

[63] Continuation-in-part of application No. 08/370,724, Jan. 10, 1995, Pat. No. 5,725,153, and a continuation-in-part of application No. 08/946,784, Oct. 7, 1997, Pat. No. 5,848, 751, which is a division of application No. 08/370,734, Jan. 10, 1995.

[51] Int. Cl.[7] .................................................. A61M 16/00

[52] U.S. Cl. ........................................ 239/102.1; 239/420

[58] Field of Search ................................ 239/102.1, 420, 239/424, 434.5, 423

[56] References Cited

U.S. PATENT DOCUMENTS

| | | | |
|---|---|---|---|
| Re. 25,744 | 3/1965 | Drayer | 239/4 |
| Re. 33,642 | 7/1991 | Lester . | |
| 2,887,181 | 5/1959 | Dillon | 185/55 |
| 2,966,312 | 12/1960 | Wilson, Jr. et al. | 239/338 |
| 3,108,749 | 10/1963 | Drayer | 239/102 |
| 3,421,699 | 1/1969 | Babington et al. . | |
| 3,790,079 | 2/1974 | Berglund et al. . | |

(List continued on next page.)

FOREIGN PATENT DOCUMENTS

| | | | |
|---|---|---|---|
| 35-11621 | of 0000 | Japan . | |
| 56-1-2959 | 8/1981 | Japan | B05B 7/02 |
| 58-40165 | 3/1983 | Japan | B05B 3/14 |
| 5138080 | 6/1993 | Japan | 239/102.1 |
| 2 203 241 | 10/1988 | United Kingdom | G01N 1/28 |

OTHER PUBLICATIONS

Direct Injection Nebulization for Inductivity Coupled Plasma Mass Spectrometry—Wiederin et al., Anal. Chem. 1991, 63, 219–225.

Spatially Resolved Measurements of Size and Velocity Distributions of Aerosol Droplets from a Direct Injection Nebulizer—Shum et al., Appl. Spectros., vol. 47, No. 5, 1993.

(List continued on next page.)

*Primary Examiner*—Matthew C. Graham
*Attorney, Agent, or Firm*—Todd Deveau; Troutman Sanders LLP

[57] ABSTRACT

An oscillating capillary nebulizer with electrospray which is capable of nebulizing a liquid sample flow at microflow and normal liquid flow rates. The oscillating capillary nebulizer with electrospray comprises a pair of coaxial capillary tubes which are friction-fit mounted by way of peek tubing ferrules. A source of electric potential is connected to the inner capillary for production of an electric field in the vicinity of the distal end of the inner capillary. The dimensions of the inner and outer capillary tubes are such that an annular spacing is created between the inner surface of the outer capillary tube and the outer surface of inner capillary tube. A liquid sample is introduced into the nebulizer through the inner capillary tube. A gas flow path is provided by the space between the inner and outer capillary tubes. The gas enters the gas flow path through a port in the side of the outer capillary tube. At least the inner capillary tube is made of flexible material. Preferably, the inner diameter of the inner capillary tube is small enough to provide jet flow of the liquid sample at low liquid flow rates. The gas flow velocity, which is a function of the gas flow rate and the size of the annular spacing, is sufficient to cause turbulence of the gas stream around the free end of the inner capillary tube, thereby creating instability in the system. This instability, depending on how the system is set up, will initially cause the inner capillary tube to oscillate. The oscillation causes the generation of a high frequency standing wave along a portion of the length of the inner capillary and a breakup of the liquid jet into uniform liquid drop sizes.

13 Claims, 12 Drawing Sheets

U.S. PATENT DOCUMENTS

| | | | |
|---|---|---|---|
| 4,112,297 | 9/1978 | Miyagi et al. . | |
| 4,161,281 | 7/1979 | Erb et al. . | |
| 4,209,696 | 6/1980 | Fite . | |
| 4,268,460 | 5/1981 | Boiarski et al. . | |
| 4,298,795 | 11/1981 | Takeuchi et al. . | |
| 4,300,044 | 11/1981 | Iribarne et al. . | |
| 4,403,147 | 9/1983 | Melera et al. . | |
| 4,629,478 | 12/1986 | Browner et al. . | |
| 4,638,945 | 1/1987 | Toda et al. . | |
| 4,687,929 | 8/1987 | Browner et al. . | |
| 4,728,036 | 3/1988 | Bennett et al. | 239/420 |
| 4,762,995 | 8/1988 | Browner et al. . | |
| 4,861,988 | 8/1989 | Henion et al. . | |
| 4,924,097 | 5/1990 | Browner et al. . | |
| 4,960,244 | 10/1990 | Maag et al. | 239/424 |
| 5,725,153 | 3/1998 | Wang et al. | 239/102.1 |

OTHER PUBLICATIONS

Brochure for Meinhard TR 30–C3 Nebulizer; ICP Information Newelstter, vol. 19, No. 6, 408(11/93).

Brochure for Hewlett–Packard Nebulizer.

Weiderin and Houk, Measurements of Aerosol Particle Sizes from a Direct Injection Nebulizer; Appi. Spectrosc., 45, 1408 (1991).

Olesik et al., Inductivity Coupled Plasma Optical Emission Spectrometry Using Nebulizers With Widely Different Sample Consumption Rates; Anal. Chem., 66, 2022, (1994).

Weiner, B.B., Particle and Droplet Sizing Using Fraunhoffer Diffraction.

OSCILLATING CAPILLARY NEBULIZER WITH ELECTROSPRAY

RELATED APPLICATIONS

This application is a continuation-in-part of U.S. application Ser. No. 08/370,734, filed Jan. 10, 1995 now U.S. Pat. No. 5,725,153 and a continuation-in-part of U.S. application Ser. No. 08/946,784, filed Oct. 7, 1997 now U.S. Pat. No. 5,848,751 which is a division of U.S. application Ser. No. 08/370,734 filed Jan. 10, 1995.

FIELD OF THE INVENTION

The present invention relates to a method and apparatus for generating an aerosol and, more particularly, an oscillating capillary nebulizer with electrospray which is capable of nebulizing a liquid flow at low and microflow liquid flow rates and controlling the particle size and the particle size distribution of the nebulized particles.

BACKGROUND OF THE INVENTION

Typical pneumatic nebulizers, such as the Meinhard TR 30-C3 nebulizer, operate at liquid sample flow rates of about 500 μl/min or greater. The Meinhard nebulizer consists of a rigid inner glass capillary tube drawn to a fine tip, surrounded by another glass tube drawn concentrically to a conical tip. The nebulizer operates through the interaction of a liquid stream in the inner capillary and a gas stream in the annular space-between the capillary tubes causing droplet formation. The Meinhard nebulizer suffers from a number of drawbacks, including that it tends to block up due to its converging tip. Once blocked, it is usually discarded.

Nebulizers which employ parallel coaxial tubes tend to avoid blockage problems. One such nebulizer is that of the application GB 2 203 241 to Willoughby et al. In this nebulizer velocity of the entraining gas combined with thermally induced solvent evaporation serves to cause a breakup of the liquid sample jet into liquid particles to produce an aerosol. This nebulizer is described to operate over liquid sample flow rates from 10–2000 μl/min. However, such nebulizers are not known to work well at low liquid flow rates or when the end of the inner capillary tube extends out beyond the end of the outer capillary tube. By low liquid flow rates, we mean 500 μl/min or less. This nebulizer is not described to cause an oscillation of the capillary tube by creating instability in the system, but rather describes that the aerosol is created by the combination of the entraining gas velocity and liquid sample heating. Another example of a known nebulizer which incorporates a coaxial tube arrangement is disclosed in U.S. Pat. No. 4,924,097 to Browner et al.

Another form of such a nebulizer is the direct injection nebulizer (DIN) of Wiederin et al. for inductively coupled plasma mass spectrometry (ICP/MS). Anal. Chem., 63, 219–225 (1991). Wiederin et al. discloses a DIN assembly consisting of a length of fused silica capillary tubing having a 50 μm inner diameter and a 200 μm outer diameter disposed within a stainless steel tube serving as the nebulizer. The stainless steel tube has a 250 μm inner diameter and a 1.6 μm outer diameter. Thus, a 25 μm annular space is provided between the stainless steel tube and the fused silica capillary tubing. The inner tubing is positioned to extend approximately 100 μm beyond the end of the stainless steel nebulizer tube. The DIN assembly is positioned within the converging end of the quartz injector tube of the torch for injecting sample directly into the plasma of the ICP/MS. The liquid sample flow rate was optimized at 120 μl/min. with a corresponding gas nebulizer gas pressure of 200 psi and a nebulizer gas flow rate of 1.0 μL/min. In operation, Wiederin et al. observed a slight hissing sound, like most pneumatic nebulzers, which became quite loud when the plasma was started and liquids were nebulized. Wiederin et al. comments that the precision of their nebulizer was notably poorer when positioned in a spray chamber similar to a conventional pneumatic nebulizer.

The operation of the Wiederin et al. DIN assembly has been categorized by Shum et al. See Appl. Spectrosc. 47, 575, (1993). When the Wiederin et al. DIN assembly was operated at a liquid flow rate of 100 μL/min., it was found that the inclusion of methanol as an organic modifier to a liquid water sample had a dramatic effect on the size of the aerosol droplet distribution attained, as illustrated by Shum et al. It was also observed that varying nebulizer gas flow rates from 0.3–0.9 L/min., while maintaining the liquid sample flow rate constant, had little effect on the size of aerosol droplets obtained.

It is also known in the prior art to utilize ultrasonic transducers to break up a liquid sample jet into liquid droplets. For example, U.S. Pat. No. 4,112,297, to Miyagi et al., discloses a nebulizer which includes an ultrasonic transducer used to create the particle beam. U.S. Pat. No. 4,403,147, to Melera et al., incorporates an acoustic transducer, such as a piezoelectric transducer which may be used to stimulate the probe to break up the liquid stream. An example of a nebulizer which employs an oscillating piezoelectric ceramic transducer is disclosed in U.S. Pat. No. 3,790,079 to Berglund. In such nebulizers, which operate on the basis of a transducer, the frequency of operation effects the aerosol droplet size. They also are much more expensive than a coaxial tube nebulizer.

U.S. Pat. No. 3,108,749, to Draver et al., and Reissue patent RE.25,744, to Drayer et al., are representative of other forms of pressurized air induced vibrating atomizers.

None of the above described nebulizers or atomizers are known to operate reliably at microflow liquid flow rates. By microflow liquid flow rates, we mean 100 μl/min or less and preferably below 30 μl/min. Conventional nebulizers typically operate at liquid flow rates greater than 500 μl/min. However, at such liquid flow rates the solvent delivery rate to any mass spectrometer or plasma source detector will be so great as to cause considerable source instability. Hence, a solvent removal step, through either a droplet removal chamber or a two-(or three-)stage pressure reduction skimmer device is necessary. With benchtop liquid chromatography/mass spectrometry systems (LC/MS), the relatively low pumping capacity of the source makes coupling with high flow nebulizers impractical. At liquid flow rates of about 500 μl/min or less, the conventional nebulizer becomes unsatisfactory and unreliable. The lowest liquid flow rate reported by Wiederin et al. for their direct injection nebulizer is 30 μl/min. However, they teach away from such lower flows by teaching that the liquid flow rate was optimized at 120 μl/min.

It is important to recognize the relative definitions describing the range of velocities of the liquid flow. In inductively coupled plasma (ICP) work, conventional nebulizers do well in relatively high liquid flow rates (defined here as 1–2 ml/min), but perform poorly in relatively low liquid flow rates (defined here as <100 μl/min). Conversely, the prior art oscillating capillary nebulizers (OCN), perform well at low liquid flow rates compared to other devices in the fields of ICP/AES and ICP/MS.

In reference to electrospray techniques, conventional sources use only high voltage to produce the aerosols, described below. Therefore, the sources can only handle a very low flow (i.e., microflow) rate and a very low range of flow rates (1–15 μl/min). Accordingly, it will be understood by one skilled in the art that the descriptions "low" and "high" have different meanings relative to the different techniques (ICP or electrospray).

It is known in the prior art to utilize an electrospray ionization technique which incorporates a fine capillary tube made of conducting metal attached to a high voltage source. In this technique, liquid is directed through the capillary tube in which the end is connected to one pole of a high voltage source. The end of the capillary tube is spaced from the orifice plate through which ions travel into the mass analyzer vacuum chamber. The capillary is connected to the pole of the high voltage source. The electric field generates charged droplets, and the droplets evaporate to produce ions. Examples of such a technique are disclosed in U.S. Pat. No. 4,209,696 to Fite, and U.S. Pat. No. 4,861,988 to Henion et al.

In ICP/AES and ICP/MS, an OCN is used to produce and control the aerosols from the liquid. The aerosols then enter the plasma source and get excited/ionized, and finally, signals are generated by measuring the photons (AES) or ions (MS). In conventional electrospray, a high voltage is applied on the capillary. The high voltage produces charged aerosols, which then can be directly analyzed using a mass spectrometer. Therefore, electrospray is an ionization method, and may be used as an ion source.

Yet, the conventional electrospray method has several disadvantages. Firstly, it can handle only a very small flow, typically only up to about 15 μl/min. Faster pumping produces larger droplets, thus causing the ion signal to fall off and also to become unstable. Secondly, the high voltages needed to disperse a larger liquid flow into fine droplets tend to create an electrical or corona discharge. The discharge adds complexity to the spectrum produced by the mass analyzer, causing difficulties in interpretation, and in addition, for unknown reasons, it tends to suppress the ion signals from the evaporated droplets. Other disadvantages are that dynamic range is usually less than two orders of magnitude, and that this process does not work well with additives. In addition, the electrospray method requires that the proportion of water in liquid be low, since otherwise a stream of large droplets tends to be produced. The large droplets reduce the sensitivity and also affects the stability of the ion signal, i.e. large fluctuations occur in the ion signal. Also, the prior art devices and methods tend to fail in performance and reliability as higher concentrations of water are used.

Therefore, a need exists in the art for a nebulizer which is capable of producing an aerosol at microflow liquid flow rates for employment with microflow chromatographic techniques and for use with bench top LC/MS, ICP/AES and ICP/MS instruments and which is capable of satisfactorily controlling the particle size and particle size distribution of the aerosol over wide concentration ranges of solvents and liquid flow rates, wider than those achievable with conventional electrospray methods. Accordingly, the present invention employs an inner/outer coaxial tube arrangement utilizing the electrospray technique which can meet these needs and overcome the above deficiencies.

SUMMARY OF THE INVENTION

Electrospray is an ionization technique for mass spectrometry that has the potential for producing ions even for compounds with very high mass. Since electrospray operates without the input of heat into the stray-ionization step, labile and polar samples are ionized without thermal degradation.

The combination of pneumatic nebulization in an electric field tolerates higher eluent flow rates and a higher percentage of water in the formation of a spray of charged droplets. In pure electrospray, a high electric field is required for both nebulization and charging. A second improvement over pure electrospray is that the nebulizer assistance allows a larger distance between the spray capillary and its counter electrode, which, together with the spray voltage, reduces the electric field at the tip and prevents a corona discharge even with nitrogen as the nebulizing gas.

The present invention, unlike conventional electrospray, uses the OCN to assist in the production of charged droplets by the application of high voltage. The present invention, OCN/ESI, is better than conventional electrospray with respect to flow rate ranges and water content ranges in mobile phases.

The present invention combines oscillating capillary nebulization with electrospray ionization. Accordingly, the present invention utilizes both an inner/outer coaxial tube arrangement, and means to produce an electrical field, for creating an aerosol at low and microflow liquid flow rates particularly for use with chromatographic techniques and for use with bench top LC/MS, ICP/AES and ICP/MS instruments, among others, and for controlling the particle size and particle size distribution of the aerosol.

The present invention comprises a pair of coaxial capillary tubes which are disposed in parallel to one another and which are preferably friction-fit mounted by way of PEEK tubing ferrules. The inner capillary tube comprises a conducting material, while retaining an amount of flexibility. The inner capillary's proximal end is attached to a voltage source. The dimensions of the inner and outer capillary tubes are such that an annular spacing is created between the outer surface of the inner capillary tube and the inner surface of the outer capillary tube. A rotating connector ring or fitting may be included to allow the position of the inner capillary tube to be adjusted in the coaxial directions relative to the outer capillary tube.

A source of electric potential is connected to the inner capillary for production of an electric field in the vicinity of the distal end of the inner capillary. For negative ion operation, the high voltage may be kept in the range of −2000 to −3500 volts with the preferred range being −2500 at −3000 volts, and for positive ion operation in the range of +2000 to +3500 volts with the preferred range being +2500 to +3000 volts. The actual voltage applied will vary depending upon the analyte.

A liquid sample is introduced into the nebulizer through the inner capillary tube. A gas flow path is provided by the annular space between the inner and outer capillary tubes. The gas enters the gas flow path through an opening in the side of the outer capillary tube. At least the inner capillary tube is made of a flexible material, preferably polyinide coated fused silica. This capillary may also be coated with a thin film of electrically conductive metal. The outer capillary tube may be made of either a flexible material or an inflexible material. Preferably, the inner diameter of the inner capillary tube is small enough to provide jet flow of the liquid sample at microflow liquid flow rates. The gas flow velocity, which is a function of both the gas flow rate and the size of the annular space, is sufficient to cause turbulence of the gas stream around the end of the inner capillary tube, thereby creating instability in the system. This instability, depending on how the system is set up, will initially cause the inner capillary tube to oscillate and possibly also the outer capillary tube, if the outer capillary tube is also made of a flexible material.

The position of the inner tube relative to the outer tube is not critical, and the inner tube may be extended or retracted up to about 1.25 mm from the end of the outer tube. However, optimum performance is obtained either with the two tubes approximately flush with one another, or the inner tube extending slightly beyond the end of the outer tube, depending on the gas flow rates. The oscillation causes the generation of a high frequency standing wave along a portion of the length of the inner capillary tube which then transmits the energy to the liquid stream causing the breakup of the liquid sample stream exiting the inner capillary tube into small liquid drop sizes.

In reference to the electrospray technique, as the liquid sample emerges from the inner capillary, it is subjected to a very strong electric field in the vicinity of the distal end of the inner capillary. The strong field polarizes the liquid sample at the end of the inner capillary, causing an elongated liquid filament to be formed and then normal surface tension forces produce instabilities which snap off a length of the filament to form small droplets. Inasmuch as the snapping off of the filament occurs while the filament is in the strong electric field, the droplet formed is highly charged electrically. The electric fields acting on the charged droplet tend to accelerate the droplet away from the distal end of the inner capillary.

If the liquid sample is volatile, it tends to evaporate and the droplet diminishes in size. If no charge leaks off the droplet while it is evaporating, the charge density on the surface of the droplet increases. When the surface charge density is low, the surface tension forces which tend to hold the droplet together in its spherical shape exceed the electro-repulsive forces caused by the surface density, and the droplet retains a spherical shape. However, as the droplet evaporates without loss of charge, there is a point reached where the electro-repulsive forces exceed the attractive surface tension forces, whereupon the droplets become unstable and tend to break up into two or more smaller charged droplets.

The present invention improves upon the prior art, and produces aerosol particles at higher liquid flow rates than is known possible with the prior art devices. The typical prior art electrospray nebulizers generally operate at liquid flow rates of approximately 1 μl/min. to 15 μl/min. Another type of electrospray nebulizer, disclosed in Henion et al., uses the direct interaction between gas velocity and liquid jet to cause a breakup of the liquid jet into liquid particles. By operating over a wider range of liquid flow rates than the prior art electrospray nebulizers, the OCN nebulizer with electrospray of the present invention is able to achieve greater control over particle size and particle size distribution, more uniform particle sizes and smaller mean particle sizes than before. Furthermore, the particle drop sizes found are only slightly influenced by the surface tension or viscosity of the solvents used with typical pneumatic nebulizers.

The present invention also overcomes the deficiencies of the prior electrospray devices. It allows for greater toleration of liquid flow rates, of up to 200 μl/min as opposed to 15 μl/min for the prior electrospray devices. It allows for higher water percentage in the liquid flow, up to 100%. It provides a greater dynamic range of up to 3 orders of magnitude. It is also not as limited in the inclusion of additives to the liquid.

In the preferred embodiment, the capillary tubes are replaceable in case of either breakage or blockage.

Accordingly, it is an object of the present invention to provide an oscillating capillary nebulizer with electrospray which is capable of generating aerosol at higher liquid flow rates and of higher water percentages than prior electrospray devices.

It is another object of the present invention to provide an oscillating capillary nebulizer with electrospray ionization which is capable of producing a primary aerosol distribution having smaller mean droplet sizes than prior known pneumatic nebulizers.

It is a further object of the present invention to provide an oscillating capillary nebulizer with electrospray which is capable of being used with bench top liquid chromatograph and mass spectrometer instrument systems and microflow separation techniques such as LC and CE combined with ICP/AES, ICP/MS, FT-IR, FT-MS and MS/MS.

Yet another object of the present invention is to provide an oscillating capillary nebulizer with electrospray which is capable of achieving better control over the particle size and particle size distribution of aerosol droplets generated.

It is another object of the present invention to provide an oscillating capillary nebulizer with electrospray which is capable of achieving results similar to those achieved by ultrasonic nebulizers at greatly reduced costs.

It is another object of the present invention to provide an oscillating capillary nebulizer with electrospray which is capable of operating over a wide range of liquid flow rates.

Another object of the present invention is to provide an oscillating capillary nebulizer with electrospray that significantly increases the dynamic range of measurement.

Yet another object of the present invention is to provide an oscillating capillary nebulizer with electrospray which can perform well at higher concentration percentages of water, up to utilizing 100% water.

It is yet another object of the present invention to provide an oscillating capillary nebulizer with electrospray which is effective at both atmospheric and reduced pressure.

These and other objects of the present invention will be apparent from the detailed description of the invention.

BRIEF DESCRIPTION OF THE DRAWINGS

FIG. 1(*b*) illustrates a cross-sectional side view of the oscillating capillary nebulizer of the present invention, with adjustable inner capillary position.

DETAILED DESCRIPTION OF THE INVENTION

Figure 1A:
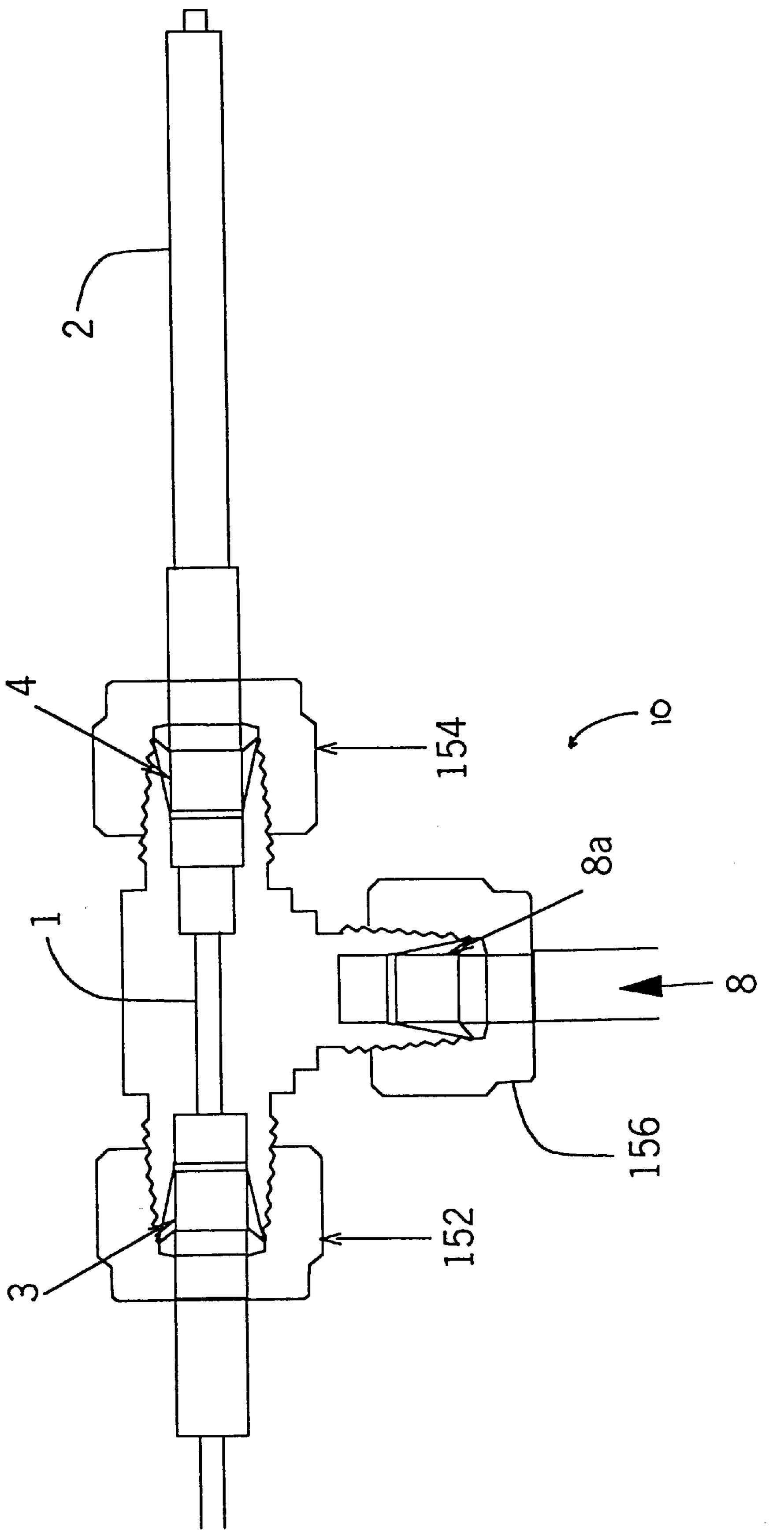
FIG. 1(*a*) illustrates a cross-sectional side view of the oscillating capillary nebulizer used in electrospray of the present invention.
Figure 1B:
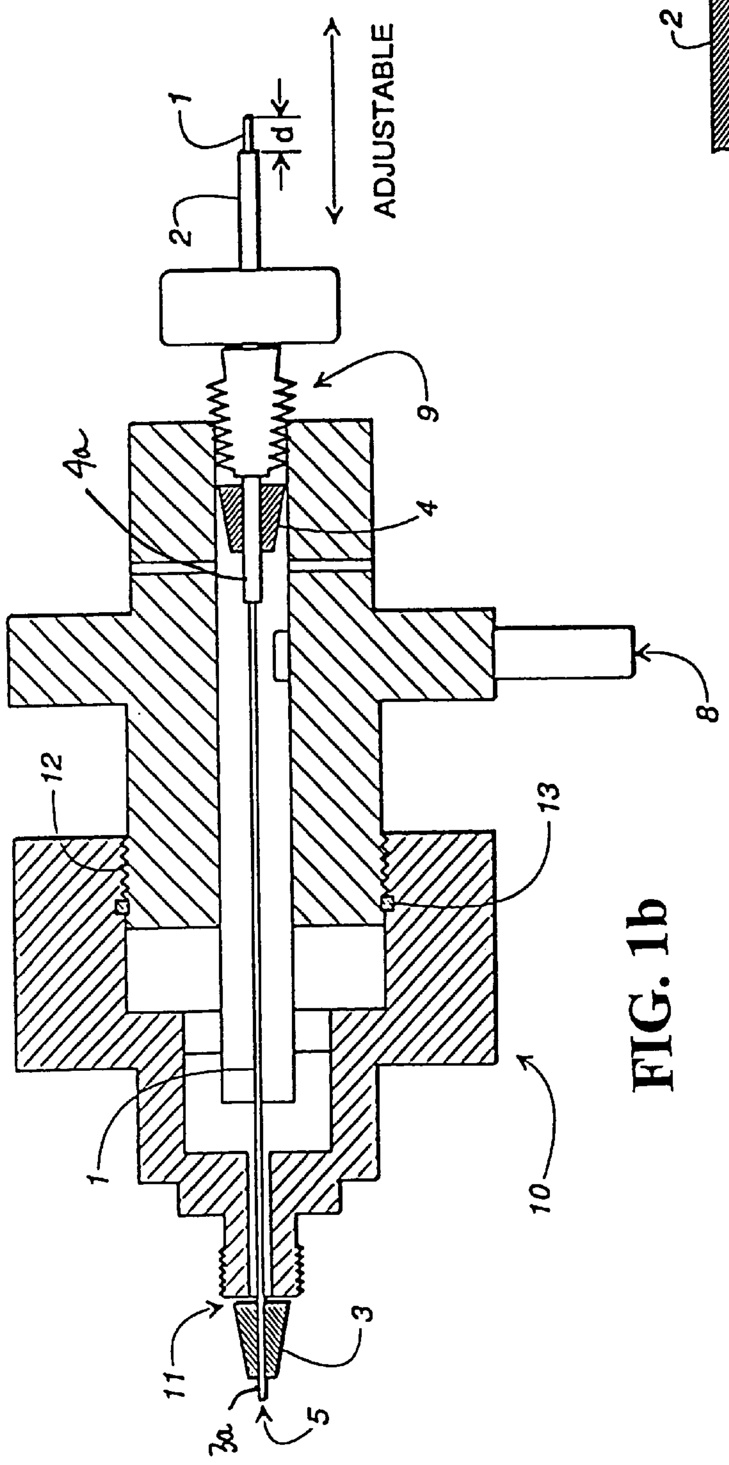

FIGS. 1*a* and 1*b* are two embodiments of the present invention 10. The two embodiments are generally similar, and described in reference to FIG. 1*b* in detail below.

Figure 2:
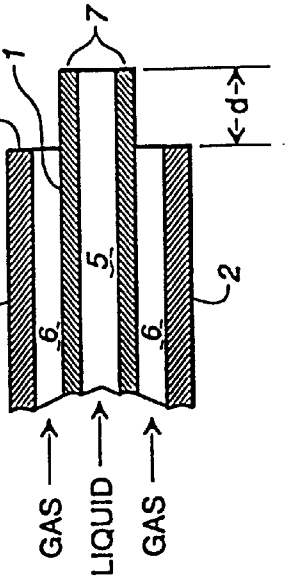
FIG. 2 illustrates a cross-sectional view of the coaxial arrangement of the inner and outer capillary tubes of the present invention.

The configuration of FIG. 1*a* differs from that of FIG. 1*b* in that post 8 provides a gas inlet to annular space 6, shown in FIG. 2 via a tee 150, preferably a Swagelok™ Union Tee. Additionally, ferrules 3, 4, 8*a* friction—fit capillary tubes 1, 2 and port 8, respectively, which ferrules 3, 4, 8*a* are held secure by nuts 152, 154, 156, respectively. Further, as described below, as shown in FIG. 1*a*, tubes 1, 2 are left in the same relative position after initial adjustment.

As shown in FIGS. 1(*b*)-3, the oscillating capillary nebulizer with electrospray 10 of the present invention is comprised of a pair of coaxial inner and outer capillary tubes 1, 2. The capillary tubes are friction-fit mounted by way of PEEK tubing ferrules 3 and 4 near their proximal ends 3*a* and 4*a*, respectively. This fitting allows for interchangeability and replacement of capillary tubes. Liquid sample introduction, generally from a liquid chromatography, is provided by liquid flow path 5 via the inner capillary tube 1. A gas flow path is provided by the annular space 6 between the outer diameter of the inner capillary tube 1 and the inner diameter of the outer capillary tube 2. The gas enters the gas flow path through a port 8 in the side of the outer capillary tube. At least the inner capillary tube 1 is made of a flexible material, preferably polyimide coated fused silica from Polymicro Technology, Inc., which adds flexibility and makes the tubing less brittle. The outer capillary tube 2 may also, but need not, be made of a flexible material. The dimensions of the inner capillary tube 1 are such that a flow of the liquid sample can be provided at flow rates as low as 50 μl/min. and less and also up to 200 μl/min.

A connector 11 is shown for allowing connection of the liquid sample input of the nebulizer to a ZDV union. The nebulizer is further constructed with a rotating connector ring 12 sealed by O-ring 13.

A source 100 of the electrical potential is connected to the inner capillary tube 1. For negative ion operation, the inner capillary tube 1 may be kept in the range of −2000 to −3500 volts and preferably in the range of −2500 to −3000 volts; and for positive operation in the range of +2000 to +3500 volts, preferably in the range of +2500 to +3000 volts. The actual voltage applied will vary dependent upon the analyte involved.

With reference to FIG. 1(*a*), the inner and outer tubes 1, 2 are left in the same relative position after initial adjustment. With reference to FIG. 1(*b*), the inner and outer capillary tubes 1, 2 are arranged to provide relative movement between them in the axial directions. Preferably, a rotating connector ring or fitting 9 allows the outer capillary tube 2 to be moved in the axial direction such that the distance that the distal end 40 of the outer capillary tube 2 extends in relation to distal end 7 of the inner capillary tube 1 can be adjusted.

Figure 3:
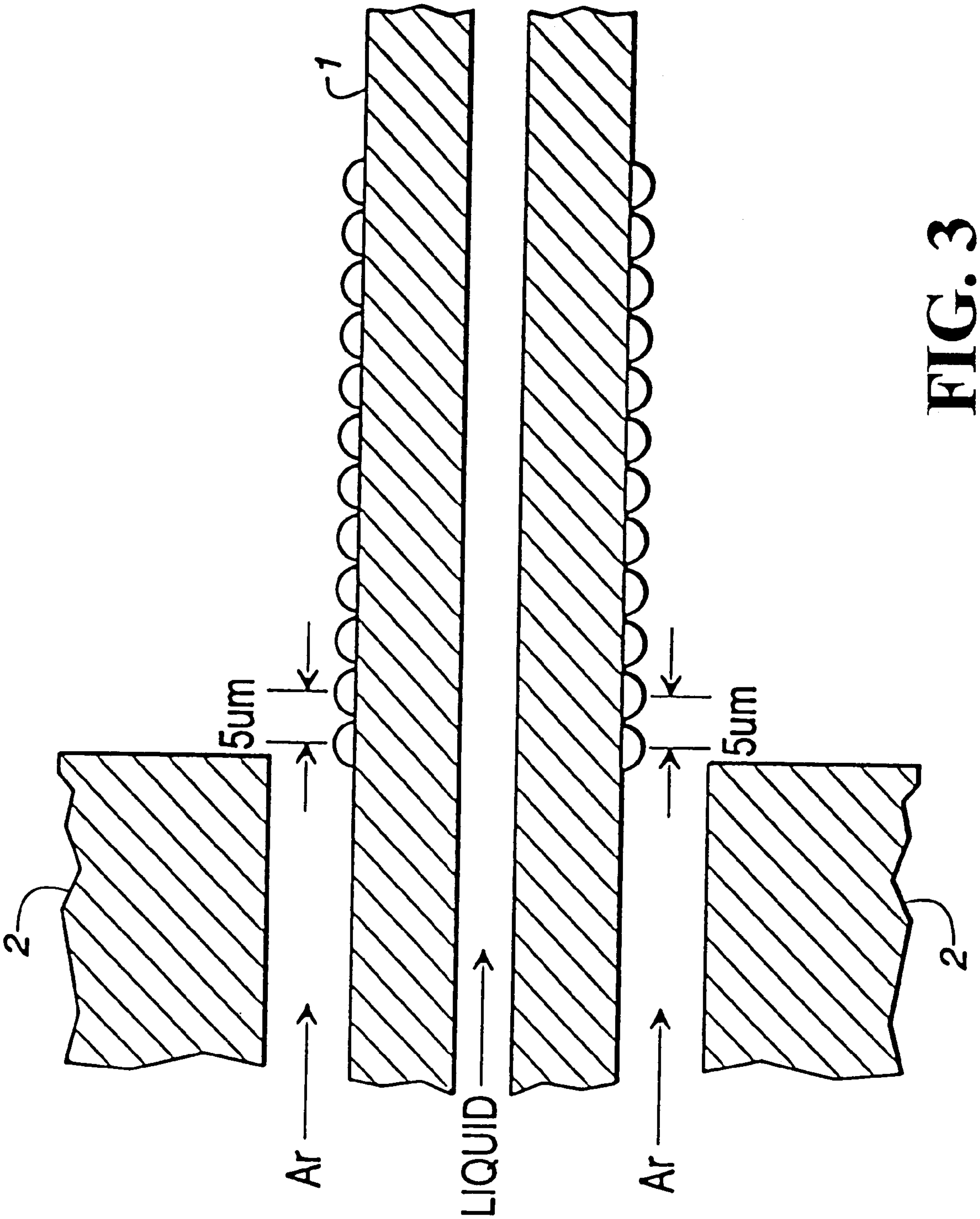
FIG. 3 illustrates a trace of the ultrasonic wave observed on the inner capillary tip of the oscillating capillary nebulizer with electrospray of the present invention.

In operation, the gas flow velocity must contain sufficient kinetic energy to cause turbulence of the gas stream around the distal end 7 of the inner capillary tube and impart instability in the system. This gas flow velocity is a function of the gas flow rate and the size of the annular space 6 between the capillary tubes. In order to create this instability, sufficient gas velocity for a particular gas is needed to cause the inner capillary tube to oscillate and generate an ultrasonic standing wave along the axial direction of at least a portion of the inner capillary tube, as illustrated in FIG. 3. This instability will also cause the inner capillary tube to transversely oscillate at a low frequency, and depending on how the system is set up, may also cause the outer capillary tube to oscillate if also made of a flexible material. The oscillation of the inner capillary tube is observable in both the transverse and longitudinal directions. The oscillation in the transverse direction is typically in the range of 200 Hz to 1400 Hz and is audible. However, it is the longitudinal oscillation that appears to generate the standing wave. The oscillation is in the megahertz to tens of megahertz range and is inaudible. In one set of conditions the observed wavelength of the longitudinal oscillation was about 5 μm. The longitudinal oscillation of the inner capillary tube causes a breakup of the liquid jet into uniform liquid drop sizes. The oscillating capillary nebulizer with electrospray of the present invention is capable of operating to produce aerosol over a liquid microflow rate range of up to 200 μl. The gas flow rate range is generally from 0.5 liters/min. to 1.0 liters/min. The instability of the inner capillary tube or inner and outer capillary tubes is a function of the location of the distal end 7 of the inner capillary tube 1 with respect to the distal end 40 of outer capillary tube 2, the dimensions of the inner and outer capillary tubes 1 and 2, and the gas and liquid flow rates.

Figure 4:
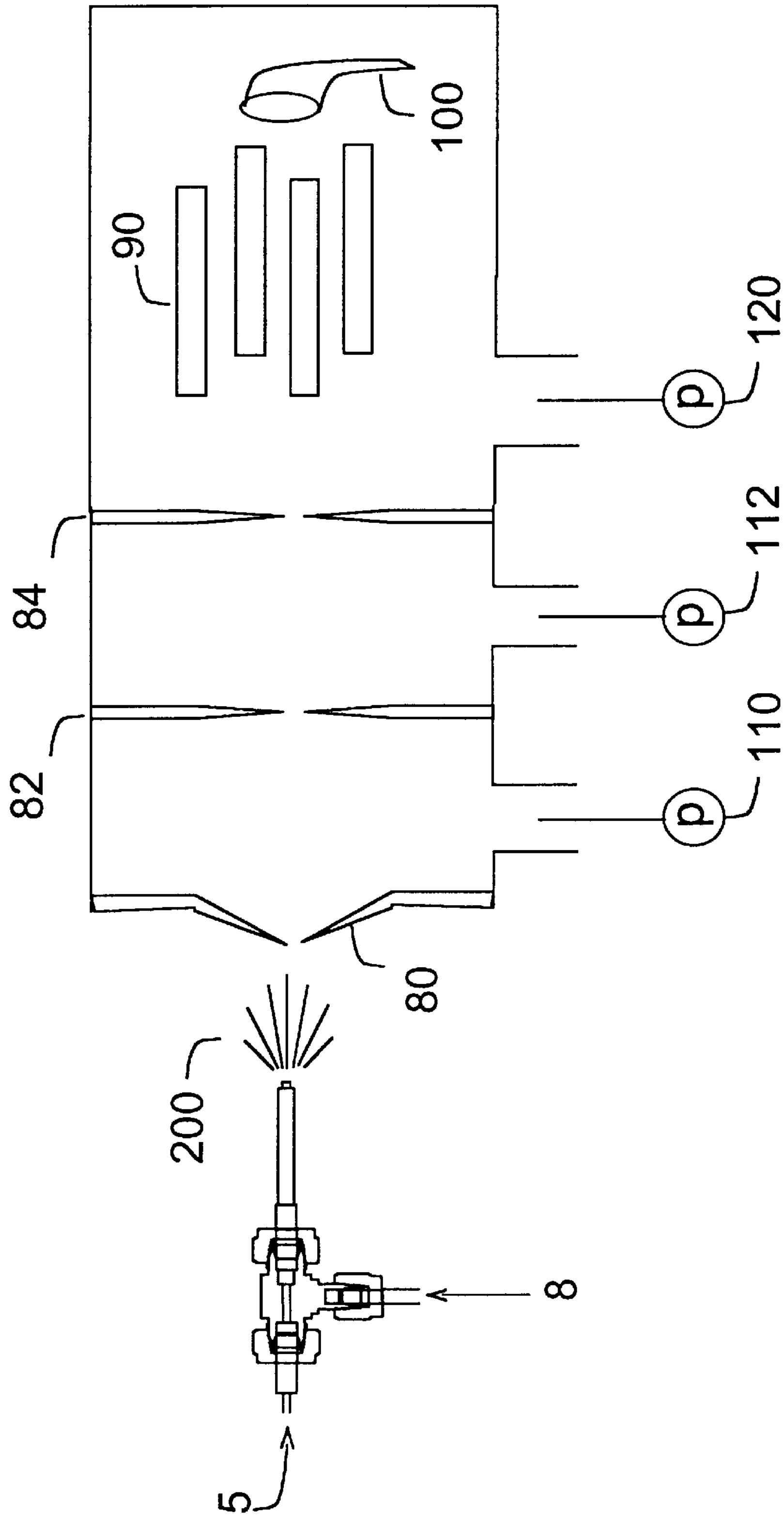
FIG. 4 illustrates the oscillating capillary nebulizer with electrospray of the present invention combined with an LC/MS system (Extrel Benchmark).

FIG. 4 illustrates the oscillating capillary nebulizer with electrospray ionization of the present invention interfaced with a Benchmark™ mass spectrometer for LC/MS work. The interface consists of a nozzle 80 and two skimmers 82, 84 which are all made of stainless steel. The aerosols 200 generated by the oscillating capillary nebulizer are introduced into the mass spectrometer through the nozzle 80, first and second skimmers 82, 84, which are all biased at different potentials to create electric gradient to guide the charged aerosols. The mass spectrometer uses a quadruple 90 as its mass analyzer and an electron multiplier 100 as the signal generator. The interface region is maintained at vacuum pressure by a pair of rotary vacuum pumps 110, 112 and the mass analyzer region is maintained at vacuum pressure by a turbomolecular pump 120. In order to maintain the desired vacuum pressure in the mass analyzer region, it may be necessary to use more than one such pump.

Figure 5:
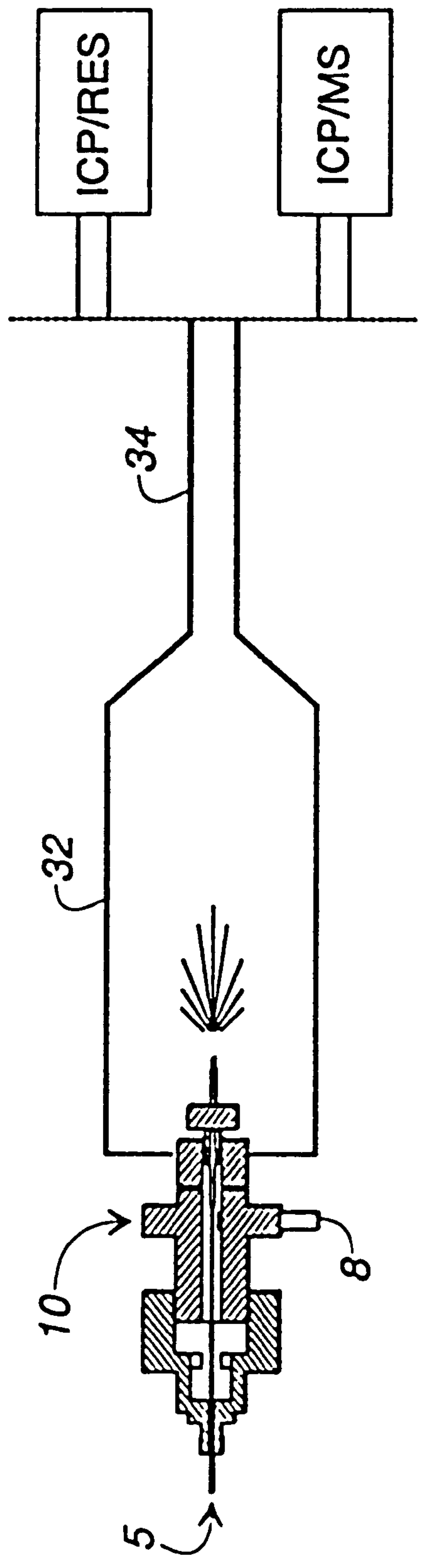
FIG. 5 illustrates the oscillating capillary nebulizer of the present invention and an interface for either an ICP/AES or an ICP/MS system.

In FIG. 5, the oscillating capillary nebulizer 10 of the present invention is shown with an interface for either an ICP/AES or ICP/MS system for operation at atmospheric pressure. In this application, the aerosol of the oscillating capillary nebulizer is introduced into a spray chamber 32 which is coupled with transfer tubing 34 leading to either the ICP/AES or the ICP/MS system. The OCN can also be used as an interface between micro LC to ICP-AES or ICP-MS.

EXPERIMENTAL

The oscillating capillary nebulizer with electrospray of the present invention was constructed as described above with reference to FIGS. 1(*a*) and (*b*) with lengths of the liquid and gas capillary tubes 1, 2 being 80±10 mm. and 30±10 mm., respectively. In the fixed version of the OCN, as shown in FIG. 1(*a*), the relative capillary positions are established by adjustment of the individual capillaries, which are then locked in position. In the adjustable version of the OCN, as shown in FIG. 1(*b*), the rotating connector fitting 9 was used, when necessary, to adjust the position of the outer capillary tube 2 relative to the one in the axial direction relative to the position of the inner capillary tube 1. The adjustable distance between the tips of both capillaries was in the range of −2 mm. to +3 mm.; the negative values indicating that the inner capillary tube was retracted inside the gas capillary tube, and the positive values indicating that the distal end of the liquid capillary tube was extending beyond the distal end of the gas capillary tube. The capillary tubes were friction-fit mounted by PEEK tubing ferrules allowing for easy change of either or both capillary tubes. In this way, the four diameters of the capillary tubes, namely, the inner and outer diameters of each tube could be manipulated, simply by swapping out the capillary tubes.

The liquid samples were introduced into the liquid capillary tube 1 by a Hewlett-Packard Model 1090 Liquid Chromatography Pump which is capable of delivering continuous liquid flows with 1 μl/min. resolution. At liquid flow rates of 10 μl/min. or less to cancel pulsation of the pump, a short length of 20 μm i.d. silica capillary tube was placed in line between the pump and the liquid capillary 1. A Matheson mass flow controller Model 8270 was used to control the nebulizer gas flow rate. The back pressure for the gas flow rate was 150–200 psi for the oscillating capillary nebulizer of the present invention, unless otherwise specified.

A Malvern (Southborough, Mass.) 2600c Droplet and Particle Sizer was used for measuring aerosol drop size distributions. This instrument consists of a helium/neon laser beam, a receiver lens, and a series of 31 semi-circular concentric annular detectors in addition to a central detector. The operating principle of the Malvern system is based on the Fraunhoffer diffraction theory. B. B. Wiener, "Particle and Droplet Sizing Using Fraunhoffer Diffraction," in Modern Methods of Particle Size Analysis, H. G. Barth, ed. John Wiley & Sons, N.Y. (1984). By measuring the scattering of the small forward angle, histogram plots of volume percent versus particle size of aerosol can be provided. Unfortunately, the measurable particle range is limited to 1.9 μm to 176 μm by this theory. Especially for 1–2 μm particles, the errors can be 20% or more. In spite of these limitations, laser Fraunhoffer scattering systems have been used extensively for measuring aerosol from atomic spectrometric systems and have inherent advantages. See also, D. R. Wiederin and R. S. Houk, Appl. Spectrosc., 45, 1408, (1991); and J. W. Olesik, J. A. Kinzer and B. Harkelroad, Anal. Cheim, 66, 2022, (1994). It is non-intrusive, precise, absolute, and fast.

The Fraunhoffer particle sizer provides a great deal of information about aerosol size distribution. To relate the aerosol properties to the analytical atomic spectrometric signals, two important parameters are used: the Sauter Mean Diameter ($D_{3,2}$) and the drop size distribution. The Sauter mean diameter is a measure of a total volume of particles in a distribution compared to the surface area. Mathematically, it can be expressed as the following formula:

$$D_{3,2}=\{\Sigma d_j^3 N_j / \Sigma d_j^2 N_j\}$$

where $d_a$ is the jth diameter and $N_j$ is the number of particles of diameter $D_j$.

For a given analyte concentration the analyte mass contained in the aerosol is directly proportional to aerosol volume. Moreover, the evaporation and vaporization rates of particles are inversely related to the volume-to-surface area ratios. The lower the $D_{3,2}$, the faster evaporation and vaporization occur, resulting in a higher signal. The drop size distribution obtained by the Fraunhoffer scattering is percent volume distribution which can be readily transposed into a mass distribution and knowing the solvent and analyte density.

In our experiments, a lens of 63 mm focal length was used and particle size range observed was 1.22 to 118 μm. The Malvern instrument was operated using the "independent mode" option. The primary aerosols were perpendicularly introduced into the helium/neon laser beam directly from the nebulizer at a distance of 14 mm for all measurements. Each measurement was made in triplicate and all data were an average of the three measurements. The information provided by the particle sizer is percent volume based on drop-size distribution. Argon was used as the nebulizer gas for all nebulizers. Distilled de-ionized water, and methanol were used as solvents.

Figure 6:
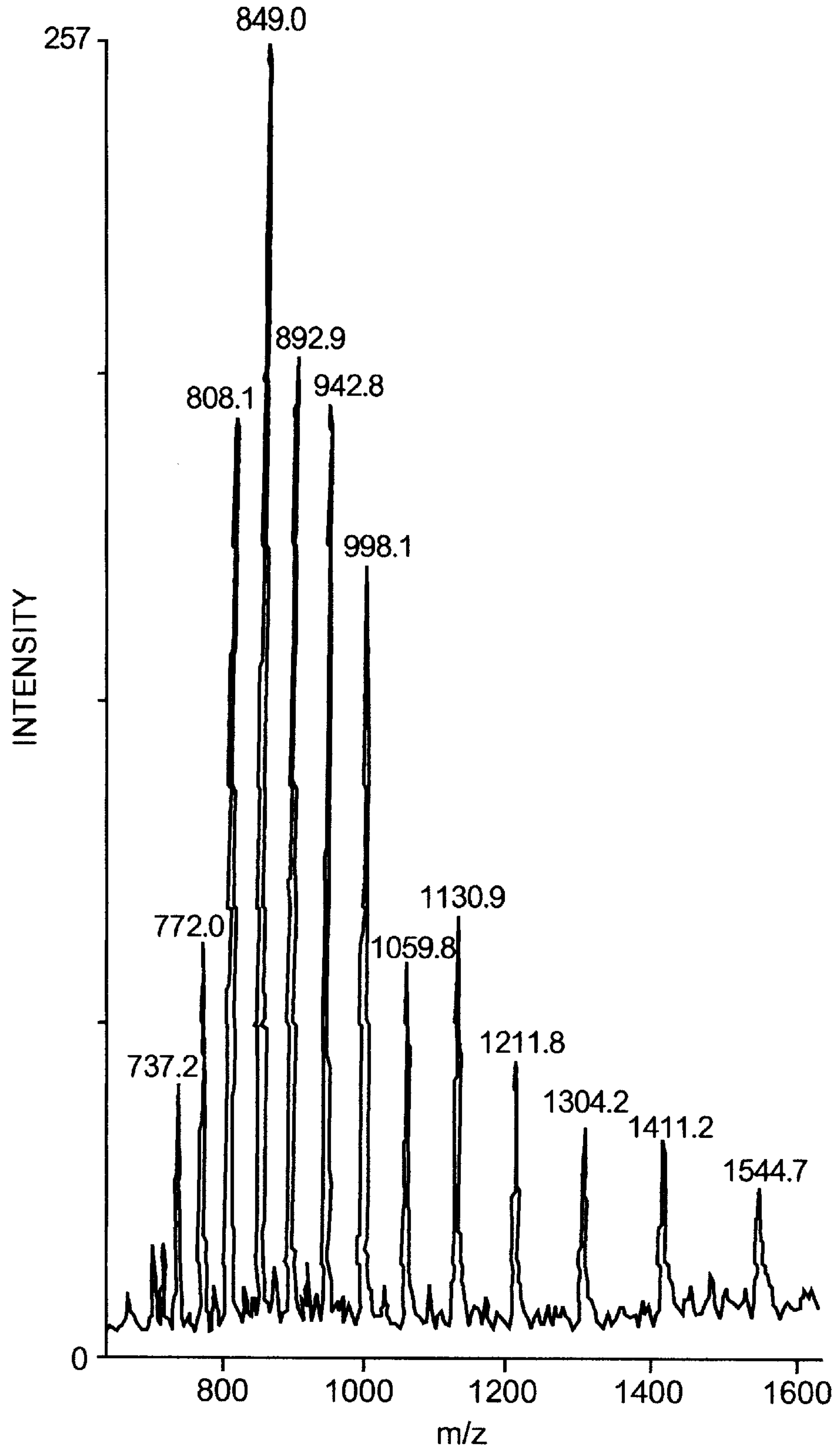
FIG. 6 illustrates the mass spectrum of horse heart myoglobin with a standard ESI source.
Figure 7:
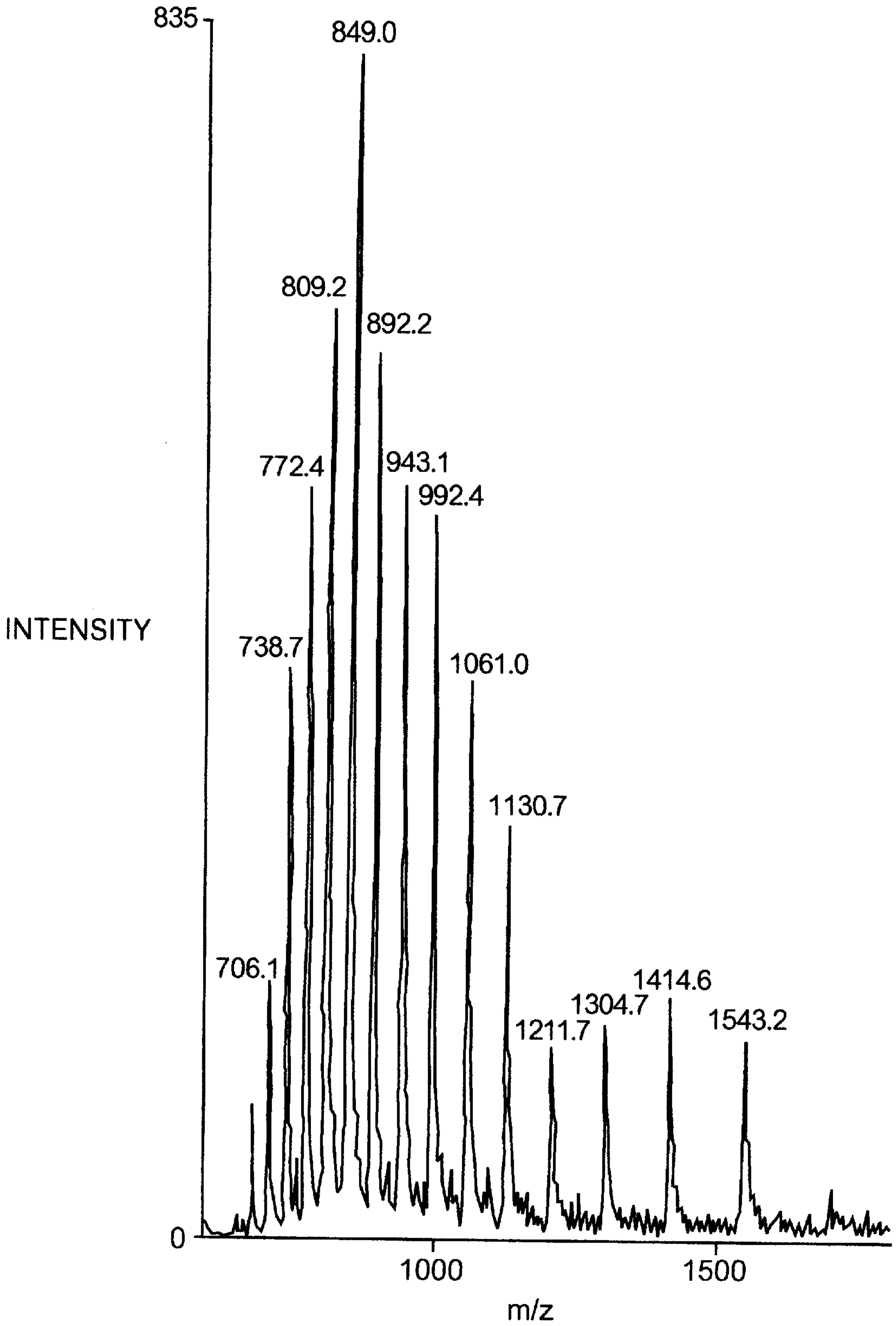
FIG. 7 illustrates the mass spectrum of horse heart myoglobin (OCN/ESI).

FIGS. 6 and 7 illustrate the ability of the oscillating capillary nebulizer (OCN) of the present invention including electrospray injection (ESI) to generate standard electrospray mass spectra. FIG. 6 is a mass spectrum of horse heart myoglobin obtained from a conventional electrospray source. FIG. 7 is a mass spectrum of the same compound obtained from OCN/ESI. The instrument parameters of acquiring data are the same for the two spectra: 50:50 Methanol; water with 1% acetic acid as the solvent; and the concentration of myoglobin was 5 μM. The spectrum produced by OCN/ESI correlates closely with that from conventional electrospray source in terms of peak relative intensities and mass positions. Therefore, this shows the ability of OCN/ESI to generate standard electrospray mass spectra without distorting the appearance of the spectra.

Figure 8:
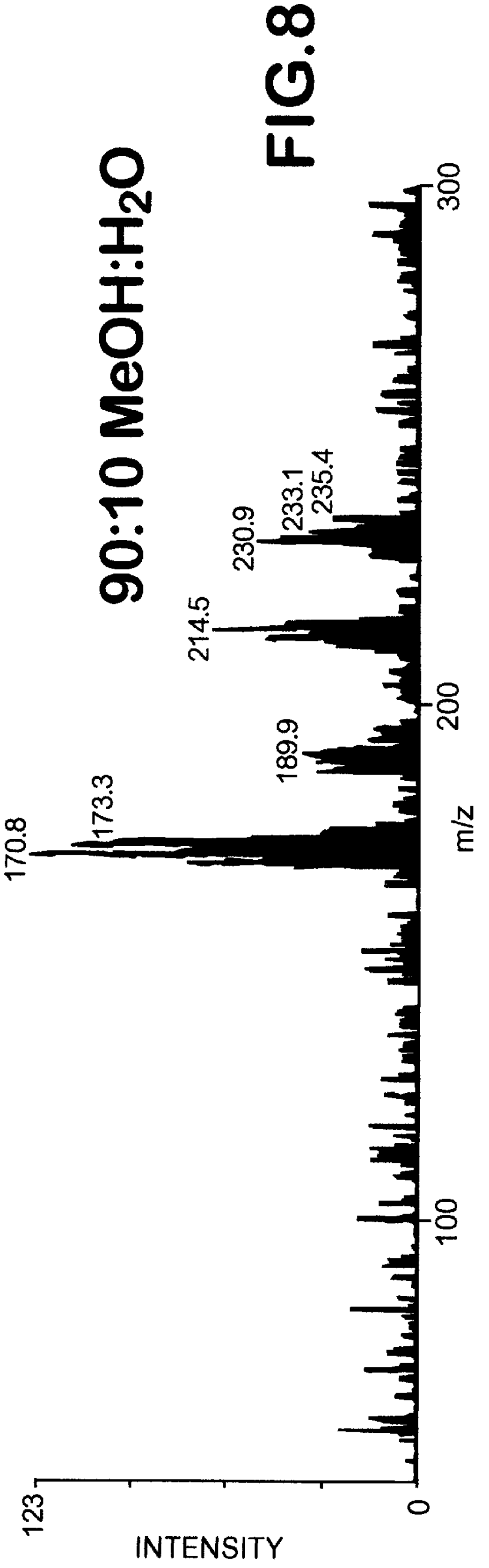
FIG. 8 illustrates the mass spectrum of $Cd(NO_3)_2$ in 10% water.
Figure 9:
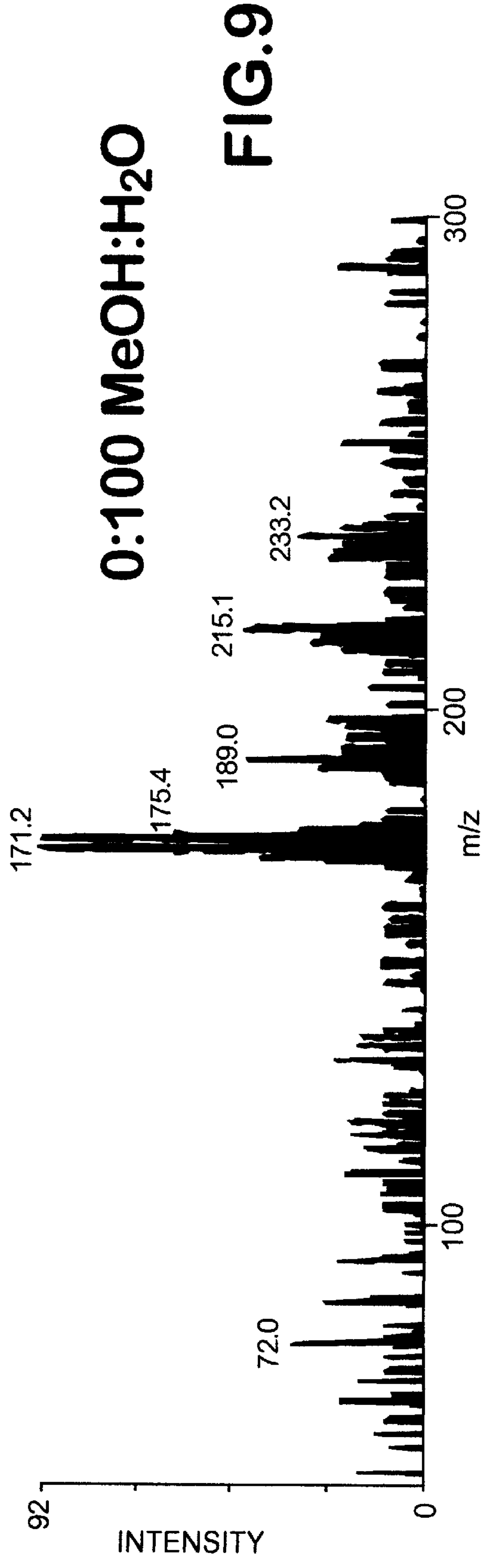
FIG. 9 illustrates the mass spectrum of $Cd(NO_3)_2$ in 100% water.

FIG. 8 shows that OCN/ESI cannot only produce electrospray spectra in organic solvent of 90% methanol and 10% water, as do conventional ESI sources, but, as shown in FIG. 9, it can also generate spectra in 100% aqueous solution, in which conventional electrospray sources do not perform well. As can be observed, the consistency of the spectra by OCN/ESI from both organic and aqueous solutions is very good.

Figure 10:
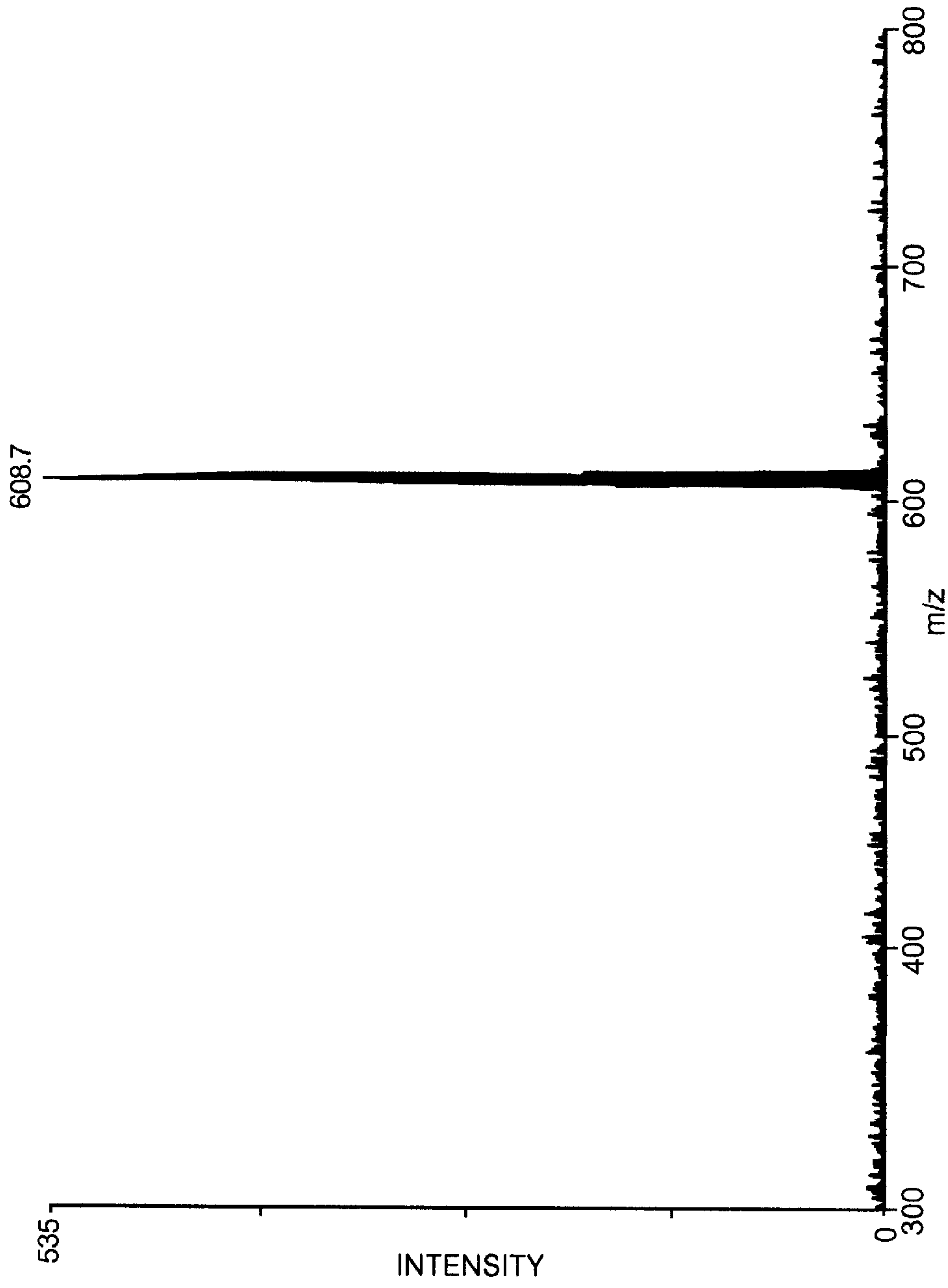
FIG. 10 illustrates the mass spectrum of reserpine (OCN/ESI).

FIG. 10 is the OCN/ESI spectrum for the compound reserpine. Reserpine was the model compound to test the quantification aspect of the OCN/ESI because it has a very clean electrospray mass spectrum with the molecular ion (m/z=609) as the only significant peak. The single ion monitoring (SIM) data acquisition mode was used to investigate the ion signals from this single mass and the results of FIGS. 11–13 are all from this peak of reserpine.

Figure 11:
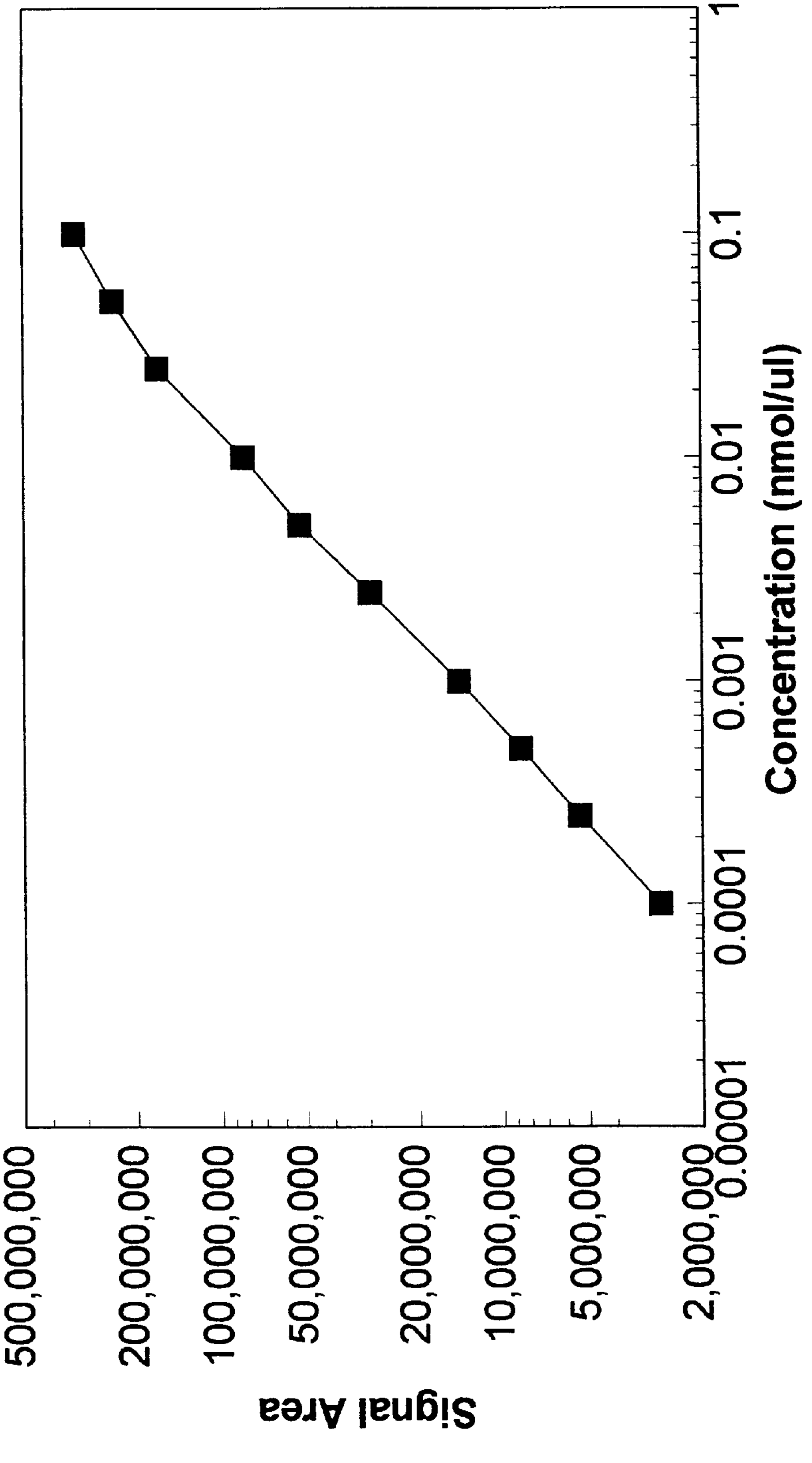
FIG. 11 illustrates the reserpine signal with respect to concentration.

FIG. 11 is a calibration curve for the reserpine signal versus its concentration using a solvent of 80% methanol and 20% water. The linear range in a log-log plot is more than three orders of magnitude. This is much better than those from conventional electrospray sources, which usually have a range of two orders of magnitude.

Figure 12:
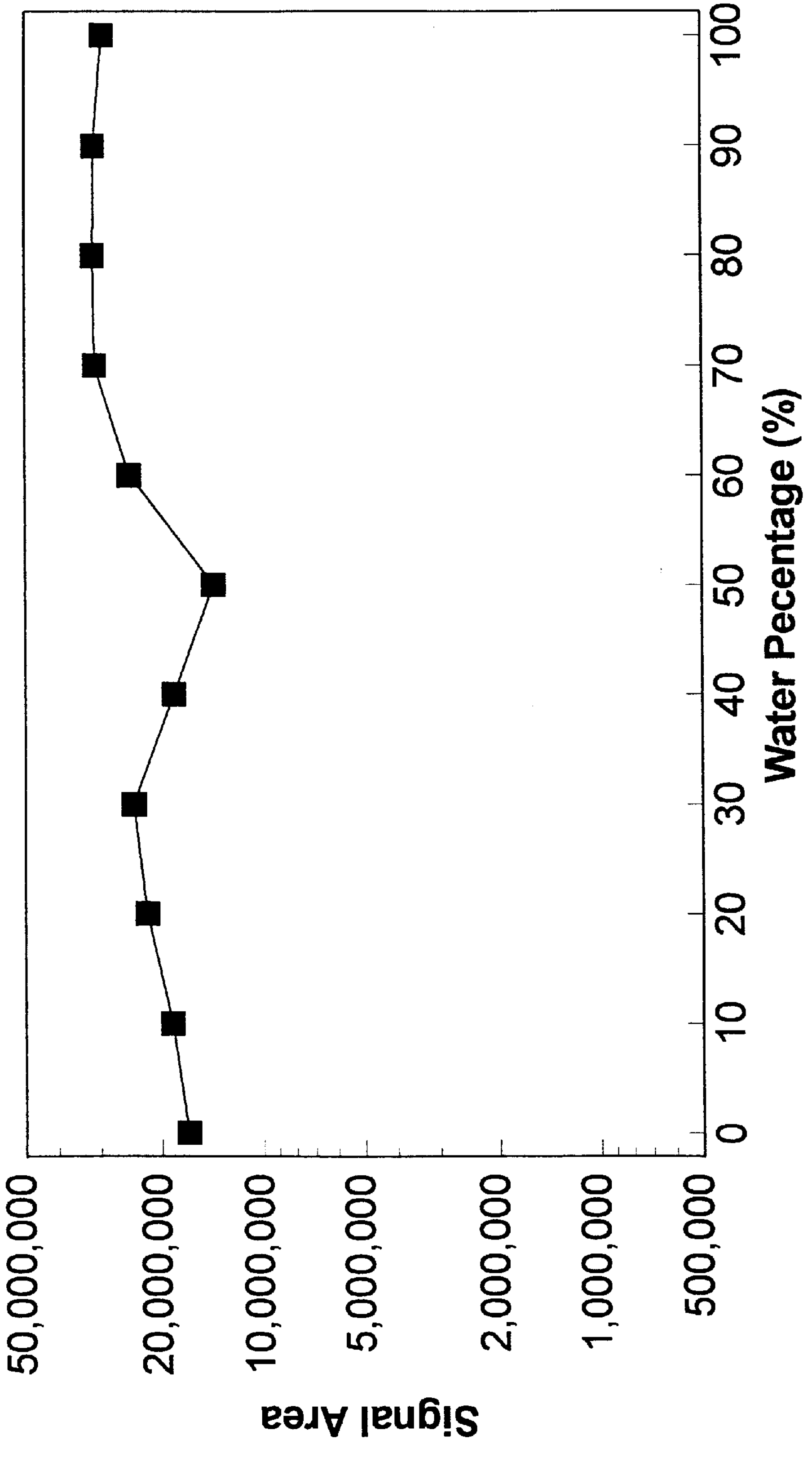
FIG. 12 illustrates the reserpine signal with respect to water percentage.

FIG. 12 is the graph of the reserpine signal versus percentage of the water in the solvent including 100% to 0% methanol. This also illustrates the ability of OCN/ESI to work in different solvents without major changes in signal. The water percentages are from 0 to 100%, and the signals remained stable; this is highly desirable in gradient liquid chromatography applications.

Figure 13:
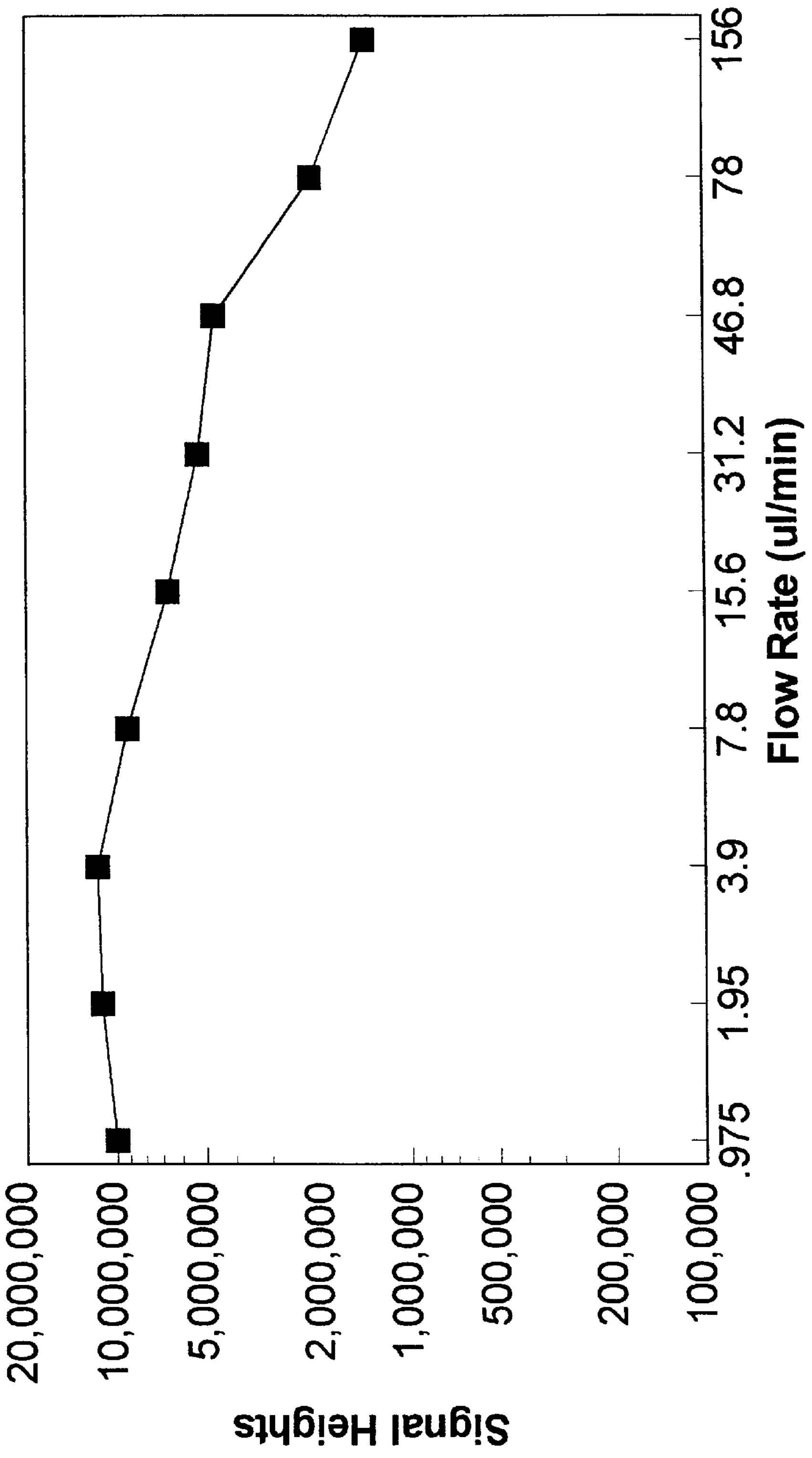
FIG. 13 illustrates the reserpine signal with respect to water to flow rate.

FIG. 13 addresses the ability of OCN/ESI to handle much higher liquid flow rates than conventional electrospray sources. Conventional sources usually require a solvent flow rate of less than 15 μl/min and are incompatible with flow rates of standard BPLC (high performance liquid chromatography). On the other hand, OCNIESI can handle a flow rate as high as 200 μl/min without significant loss of signals. This aspect of the present invention is a large advantage over the present, conventional sources.

From the above discussion, it can be seen that the above described oscillating capillary nebulizer with electrospray is capable of operating at microflow liquid flow rates which are significantly higher than the flow rates at which known conventional and electrospray devices may operate. Our nebulizer is also capable of producing a primary aerosol distribution having a mean droplet diameter which is smaller and more uniform than known nebulizers. Aerosol particle size and particle size distribution can be controlled by varying the dimensions of the inner and outer capillary tubes, by varying the location of the distal end of the inner capillary tube with respect to the location of the distal end of the outer capillary tube, and by varying the liquid and gas flow rates. Our nebulizer is operable over low liquid flow rates as low as 1 μl/min and less, as well as up to 200 μl/min. The preferable range for gas flow rates is approximately from 0.5 liters/min. to 1.0 liters/min. The preferred inner diameter of the inner capillary tube ranges from approximately 25 micrometers to approximately 103 micrometers. The preferred inner diameter of the outer capillary tube ranges from approximately 180 micrometers to 350 micrometers. The preferred annular spacing between the outer diameter of the inner capillary tube and the inner diameter of the outer capillary tube ranges from approximately 25 micrometers to approximately 75 micrometers. However, more important than the absolute values for these operating parameters is that the inner liquid capillary tube be made of a flexible material and that the annular spacing between the inner and outer capillary tubes in combination with the gas flow rate be such that the velocity of the gas flow imparts instability in the nebulizer causing the inner capillary tube to oscillate and generates a high frequency, ultrasonic standing wave along at least a portion of the liquid capillary tube.

Although the present invention has been described with reference to preferred embodiments, it will be apparent to those skilled in the art that variations and modifications of the present invention are within the spirit and scope of the present invention.

What is claimed is:

1. A nebulizer for nebulizing a liquid sample provided to said nebulizer, said nebulizer comprising:

a first outer capillary tube leaving an inner diameter and an outer diameter, a second flexible inner capillary tube having an inner diameter and an outer diameter, said outer diameter of said second flexible capillary tube being smaller than said inner diameter of said first capillary tube, said second capillary tube being coaxially arranged within said first capillary tube such that an annular spacing exists between the outer diameter of said second flexible capillary tube and the inner diameter of said firs capillary tube, means for mounting said second flexible capillary tube and said first capillary tube in the coaxial arrangement, said second flexible capillary tube having a distal end and a proximal end, means for creating and electrical field in the vicinity of the distal end of said second flexible capillary tube, said means for mounting having a gas flow opening formed therein for allowing gas to flow into the space between the outer diameter of the flexible inner capillary tube and the inner diameter of the outer capillary tube, said proximal end of said second flexible inner capillary tube being open for allowing a liquid sample to be introduced into said second flexible capillary tube, and wherein gas is introduced through the gas flow opening and the liquid sample is introduced through the opening in said proximal end of said second flexible capillary tube at flow rates sufficient to cause liquid being projected from said distal end of said second flexible capillary tube to be nebulized due to both said electrical field and oscillation of said second flexible capillary tube caused by the gas flow, and wherein a standing wave is generated along the axial direction of at least a portion of said second flexible inner capillary tube.

2. A nebulizer for nebulizing a liquid sample provided to said nebulizer according to claim 1 wherein said nebulizer further comprises means for effecting relative movement between said first outer flexible capillary tube and said second flexible inner capillary tube in the coaxial directions, wherein said means for effecting relative movement is connected to said first capillary tube at a location near the proximal end of said first capillary tube and to said second flexible capillary tube at a location near the proximal end of said second flexible capillary tube, said means for effecting relative movement substantially enclosing the proximal end of said first capillary tube to form a chamber within said first capillary tube, said second flexible capillary tube passing through said means for effecting relative movement to form the connection between said second flexible capillary tube and said means for effecting relative movement.

3. A nebulizer for nebulizing a liquid sample provided to said nebulizer according to claim 1 wherein said first and second capillary tubes are comprised of fused silica.

4. A nebulizer for nebulizing a liquid sample provided to said nebulizer according to claim 1 wherein said inner diameter of said second flexible capillary tube is sufficiently small to create a liquid stable flow at the liquid flow rate at which the liquid sample is introduced into said proximal end of said second flexible capillary tube.

5. A nebulizer for nebulizing a liquid sample provided to said nebulizer according to claim 1 wherein said nebulizer produces an aerosol at a liquid flow rate which extends from less than 1 μl/min up to 200 μl/min.

6. A nebulizer for nebulizing a liquid sample provided to said nebulizer according to claim 1 wherein the particle size and particle size distribution can be controlled by varying the dimensions of said first outer capillary tube and said second flexible inner capillary tube.

7. A nebulizer for nebulizing a liquid sample provided to said nebulizer according to claim 2 wherein the particle size and particle size distribution of the nebulized liquid can be varied by adjusting said means for effecting relative movement to thereby vary the distance between the distal end of said first outer capillary tube and the distal end of said second flexible inner capillary tube.

8. A nebulizer for nebulizing a liquid sample provided to said nebulizer according to claim 1 wherein the particle size and particle size distribution of the nebulized liquid can be varied by changing the liquid and sample gas flow rates.

9. A method of nebulizing a liquid sample comprising the steps of:

(a) mounting a second flexible inner capillary tube inside of a first outer capillary tube in a coaxial relationship, said first outer tube having a and inner diameter, and outer diameter, an outer diameter, a proximal end and a distal end wherein said outer diameter of said second flexible inner capillary tube is smaller than the inner diameter of said first outer capillary tube such that an annular spacing exists between the outer diameter of said second flexible inner capillary tube and the inner diameter of said first outer capillary tube;

(b) creating and electrical field in the vicinity of the distal end of said second flexible inner capillary;

(c) introducing the liquid sample into said second flexible inner capillary tube at a predetermined liquid flow rate such that the liquid sample flows toward the distal end of said flexible inner capillary tube; and (d) introducing a gas into the annular spacing at a predetermined gas flow rate sufficient to cause liquid being projected from said distal end of said second flexible inner capillary tube to be nebulized due to both said electrical field and oscillation of said second flexible inner capillary tube caused by the gas flow.

10. A method for nebulizing a liquid according to claim 9, wherein said first outer capillary tube is flexible.

11. A method of nebulizing a liquid according to claim 9 wherein said gas is selected from the group consisting of argon, air, helium, nitrogen and oxygen.

12. A method of nebulizing a liquid according to claim 9 wherein said nebulizer produces an aerosol at a liquid flow rate which extends from less than 1 $\mu$l/min up to 200 $\mu$l/min.

13. A method of nebulizing a liquid according to claim 9 wherein said gas flow rate is between 0.5 liters/min. and 1.0 liters/min.

* * * * *